United States Patent [19]

Thiel et al.

[11] Patent Number: 5,679,144
[45] Date of Patent: Oct. 21, 1997

[54] POWDER COMPOSITION FOR THE PREPARATION OF AN OPAQUE DENTAL PORCELAIN IN THE FORM OF A PASTE

[75] Inventors: Norbert Thiel, Bad Säckingen; Kerstin Herbst, Bensheim, both of Germany

[73] Assignee: Vita Zahnfabrik H. Rauter GmbH & Co., Bad Sackingen, Germany

[21] Appl. No.: 659,986

[22] Filed: Jun. 7, 1996

[30] Foreign Application Priority Data

Aug. 6, 1995 [EP] European Pat. Off. ............. 95108803

[51] Int. Cl.$^6$ .................. A61C 13/00; C03C 1/04; C03C 3/091
[52] U.S. Cl. ............... 106/35; 501/17; 501/64; 501/66; 501/67; 501/70; 501/74
[58] Field of Search ........................ 106/35; 501/17, 501/64, 66, 67, 70, 74

[56] References Cited

U.S. PATENT DOCUMENTS 4,879,136  11/1989  Pölz ........................... 106/35
5,009,709  4/1991  Ibsen et al. ................. 106/35

*Primary Examiner*—Melissa Bonner
*Attorney, Agent, or Firm*—Jacobson, Price, Holman & Stern, PLLC

[57] ABSTRACT

A powder composition for the preparation of an opaque dental porcelain, containing as its components
  one or more feldspar frits consisting of a number of feldspar frits of different chemical compositions and different physical properties;
  $CeO_2$ as the opacifier, optionally additional opacifiers; and
  optionally pigments.

15 Claims, No Drawings

POWDER COMPOSITION FOR THE PREPARATION OF AN OPAQUE DENTAL PORCELAIN IN THE FORM OF A PASTE

The present invention pertains to a powder composition for the preparation of an opaque dental porcelain and a powder mixture in the form of a paste.

Dental prostheses, such as dental crowns or caps and bridges, are often prepared from a metal framework which is lined with various materials. Widely used are ceramic-lined restorations which highly satisfy medical and aesthetic requirements. In particular, there has been known a multi-layer structure of the lining material on the metallic base. As the first layer, a so-called opaque layer is frequently coated on the metal framework of the restoration in order to conceal the metal color of the base framework.

From EP 0 518 454 A2 and the prior art documents cited therein, there can be seen, for instance, that the use of larger amounts of zirconium dioxide as an opacifier in glass powders results in compositions which have been shown to be useful as opaque dental porcelains. The opaque dental porcelains presented therein consist of the glass powder as the base composition and the zirconium dioxide as the opacifier which is incorporated in larger quantities. It is essential according to EP 0 518 454 that from 10 to 60% by weight of must be present as the opacifier. The composition may optionally be provided with pigments in order to achieve or approach a hue corresponding to the later tooth color in the first layer already. A particular drawback of the system mentioned therein is the high firing temperature of 980° C. At such temperatures, the heat resistance of some dental alloys is exceeded so that the metal framework becomes distorted upon fire-coating of the lining ceramic and thus the accuracy in fitting of the prosthetic workpiece is no longer ensured.

EP 0 280 985 also describes an opaque dental ceramic. In this system, the grain size of smaller than 40 μm adversely affects the application characteristics of the opaque ceramic. Another drawback of the system described therein is the fact that after the application of the opaque ceramic the surface has to be dusted with dusting crystals in order to obtain a good opacifying power and an even surface without cracks.

The U.S. Pat. No. 5,176,747 discloses porcelain compositions which are suitable for use as porcelain layers on metal bases for dental prostheses and have a fusion temperature of about 800° C. and below. The compositions can be used as coatings on dental prostheses made of titanium or titanium alloys since the coefficients of thermal expansion are near those of titanium and its alloys. The compositions described contain up to 3% by weight of cerium oxide.

EP-A-0 332 887 pertains to a method for the preparation of metallic/ceramic dental restorations. In order to achieve an optimum aesthetic matching of the dental restoration to the residual teeth, individual characteristics of the natural tooth to be replaced or the natural neighboring teeth are mimicked in the course of the construction of the metallic/ceramic dental restoration by specifically incorporating or admixing a ceramic paint in the dentin composition and/or enamel composition. By using the method described, the number of differently pigmented and opacified ceramic compositions required may be drastically reduced. As the opacifier in the opaque porcelain composition, the composition contains 10 to 20% of the oxides, tin oxide, cerium oxide and zirconium silicate.

U.S. Pat. No. 5,030,097 pertains to a mixture of particles, which are preferably finely dispersed as a colloidal suspension, of a rare-earth metal oxide fraction, such as cerium oxide, in a liquid. The liquid may be all water, but may also include other materials, such as acetic acid, 1.3-butanediol or methanol. The mixture is used as a wetting and suspending agent for opaque dental porcelains to primarily overcome the problem of discoloration of dental ceramic compositions when used with dental alloys containing silver.

The object of the present invention is to avoid the disadvantages mentioned and to provide an opaque dental porcelain which can be prepared simply and at low cost and which is characterized by very good application characteristics, low firing temperatures, a very good opacifying power and good adhesion to the metal. In addition, no discoloring is to be present in the ceramic-metal transition zone and on the edges of the restoration.

Surprisingly, the object of the invention is achieved by an opaque dental porcelain based on a powder composition containing as its components one or more feldspar frits, $CeO_2$ as the opacifier, optionally additional opacifiers, and optionally pigments. Said feldspar frit consists of a number of feldspar frit components of different chemical compositions. The chemical composition determines the physical properties of the feldspar frit, such as firing temperature, thermal expansion, transformation temperature and softening temperature. Thus, for example, these properties of the opaque dental porcelain to be prepared can be selectively varied by using different feldspar frits.

It has been shown to be of advantage if the feldspar frits have a maximum grain size of less than 20 μm, a $d_{50}$ of from 3 to 6 μm, and a $d_{90}$ of from 12 to 16 μm. Coarser grainings have been shown to deteriorate the processing properties.

In the frit mixture, especially metal oxides, such as $SnO_2$, $TiO_2$, $ZrO_2$ and the like, are employed as opacifiers in addition to $CeO_2$. The oxides employed as opacifiers have a purity of >99%, an average grain size of $d_{50}<1$ μm, and a maximum grain size of <2 μm, as well as a specific surface area of from 1 to 15 m$^2$/g. Oxides having different grain size distribution characteristics and/or a greater specific surface area are less suitable as opacifiers in the opaque dental porcelain paste to be prepared from the powder composition since grain size distribution and specific surface area immediately affect the application properties. Optionally, colored pigments are added to the white powder composition in order to obtain tooth-colored restorations. The colored pigments conventionally used in dentistry are added as the pigments.

Preferably, the main components of the powder composition according to the invention have the following ranges of proportional quantities:

from 30 to 65% by weight of $SiO_2$
from 2 to 6% by weight of $Na_2O$
from 3 to 15% by weight of $K_2O$
from 5 to 15% by weight of $Al_2O_3$
from 0.5 to 10% by weight of $CaO$
from 0.5 to 10% by weight of $B_2O_3$
from 0.5 to 50% by weight of $CeO_2$.

Particularly preferred is from 35 to 45% by weight of $SiO_2$, from 4 to 5% by weight of $Na_2O$, from 7 to 9% by weight of $K_2O$, from 10 to 12% by weight of $Al_2O_3$, from 2 to 3% by weight of $CaO$, and from 1 to 3% by weight of $B_2O_3$.

The powder composition may optionally contain further components wherein up to 9% by weight of $ZrO_2$, 50% by weight of $SnO_2$, and 50% by weight of $TiO_2$ are contained in the composition. Contents of $SnO_2$, $CeO_2$ and/or $TiO_2$ of from 10 to 30% by weight, and/or contents of $ZrO_2$ of from 3 to 9% by weight are preferred.

The powder composition according to the invention is worked with liquids, which may be used individually or as a mixture, to give a mixture in the form of a paste. The mixture according to the invention may optionally also contain additives. The addition of the liquids is adjusted to give a homogeneous, soft paste which can be readily applied with a brush and has a consistency similar to that of an ordinary cream. The liquids which may be used include, in particular, water (demineralized or distilled water), commercial modeling liquids for lining ceramics (e.g. Vita Omega Opaque Liquid, Vita Omega 800 Opaque Liquid), glycerol, dihydric alcohols, polyethylene glycols and/or silicone oils. Mixtures of from 1 to 3 parts of distilled water, from 15 to 21 parts of a trihydric alcohol, such as glycerol, and from 75 to 85 parts of a dihydric alcohol, such as 1,3-butanediol, are preferably employed. Also useful is a mixture of from 90 to 100 parts of 1,3-butanediol and from 2 to 7 parts of silicone oil, such as Baysilon® Oil M100, or a mixture of from 40 to 75 parts of 1,3-butanediol, from 5 to 12 parts of polyethylene glycol, such as PEG 400, from 20 to 30 parts of glycerol, and from 0.5 to 5 parts of deionized water.

In the mixture in the form of a paste according to the invention (opaque dental porcelain paste), the mixing ratios of liquid(s) to powder composition are preferably between 1:4 and 1:1. Particularly preferred is a mixture consisting of a proportion of opaque dental porcelain powder to the liquid of 7:3.

As additives, there may be used, in particular, agents for preventing segregation of powder composition and liquid (stabilizers), and preservatives.

In order to prevent segregations, i.e. separation of the solid from the liquid phase, stabilizers may be added singly or in combination. Such stabilizers may belong to the following groups of substances:

surface-active metal oxide powders having grain sizes in the nanometer range (5 to 40 nm), e.g. $SiO_2$, aerosils, $TiO_2$-P25, pyrogenic $ZrO_2$, alumina C;

small amounts of organic substances as thickening agents in amounts of from 0 to 5% by weight, preferably in amounts of from 0.05 to 1% by weight, for example, cellulose, methylcellulose and derivatives thereof, gelatine and/or alginates; and/or complexing and/or chelating agents, such as citric acid, Tween 20, etc.

In order to improve durability, commercial preservatives are added, for example, Thiomersal, Rokonsal, Acticid SPX, formaldehyde, etc.

Advantageously, the components of an opaque dental porcelain paste are machine-mixed, especially homogenized, since an invariable quality of the paste with respect to homogeneity and viscosity and thus invariably excellent application properties and processing properties are obtained thereby.

The finished paste mixture is filled in a commercial packing, in particular a glass jar or plastic box. A jar or box as the dosage form has an advantage in that if segregation occurs, the paste can simply be stirred up before use by means of a platic or glass spatula. Removing the paste directly from the jar or box with a brush has a further advantage in that only the immediately necessary amount of paste has to be drawn, which can not be ensured without difficulty when administering by means of a syringe.

Then, the opaque dental porcelain paste is applied to the metal framework of the dental restoration by means of a brush. Due to the excellent application properties and the outstanding opacifying power of the opaque dental porcelain paste, it is possible to apply very thin layers onto the metal framework. Thus, the user can save space and hence is able to prepare aesthetically demanding works.

The firing of the opaque dental porcelain paste onto the metal framework is performed in a range of temperatures of from 780° C. to 970° C. The firing temperature depends on the composition of the opaque dental porcelain powder, which, as mentioned above, may consist of feldspar frits of different compositions and can have different physical properties.

The opaque dental porcelain paste according to the invention which may be prepared from the powder composition according to the invention has the following advantages as compared to the opaque dental porcelain paste having a high $ZrO_2$ content known from EP 0 518 454 and the opaque dental ceramic material known from EP 0 280 985 which can only be used with dusting crystals:

By the use of opacifiers having a particular grain size distribution and a particular specific surface area, the properties of the powder/liquid mixture are highly affected while an excellent opacifying power is achieved. The application properties of the opaque dental porcelain according to the invention are very good and even when very thin layers are applied, a high opacifying power is achieved without employing dusting crystals. Another advantage of the opaque dental porcelain according to the invention is that it is fired onto the metal framework at firing temperatures of below 970° C. This limits or reduces the risk of distortion of the framework upon firing of the ceramic due to low heat resistance. After firing, the surface is slightly rough and has a silky gloss. Such surface properties are of considerable advantage since the subsequent dentin layer is readily applied and the bonding between the opaque layer and the dentin layer is improved. Another advantage can be seen in the presentation in a glass vessel.

The invention will now be illustrated in more detail by the following examples.

EXAMPLE 1

A mixture of crushed feldspar and mineral oxides is fused at high temperatures and quenched in water. The feldspar frit thus formed is finely ground and optionally mixed with frits of different chemical compositions. The feldspar frit prepared, which consists of 55.6% by weight of $SiO_2$, 5.4% by weight of $Na_2O$, 1.4% by weight of CaO, 11.1% by weight of $K_2O$, 15.29% by weight of $Al_2O_3$, 8.33% by weight of $TiO_2$, and 2.88% by weight of $B_2O_3$, is mixed in an amount of 77 parts by weight with 16 parts by weight of $CeO_2$ and 7 parts by weight of $ZrO_2$. A mixture is prepared from 95 parts of 1,3-butanediol and 5 parts of silicone oil (Baysilon® Oil M100). This mixture of liquids is mixed in an amount of 40 parts of liquid with 60 parts of opaque dental porcelain powder and mixed and homogenized in a sigma-shaped kneader-mixer. For this purpose, 0.02 parts by weight of methylhydroxypropylcellulose MHPC 8000 and 0.02 parts by weight of citric acid are added. To increase durability, 0.05 parts by weight of Thiomersal is added as a preservative.

An elemental analysis of the inorganic components of the opaque dental porcelain paste gives the following composition:

| | |
|---|---|
| $SiO_2$ | 40.65% |
| $Na_2O$ | 3.82% |
| $TiO_2$ | 5.74% |
| CaO | 1.03% |
| $K_2O$ | 8.02% |
| $Al_2O_3$ | 11.18% |

-continued

|      |        |
|------|--------|
| $ZrO_2$ | 6.71% |
| $SnO_2$ | <0.01% |
| $CeO_2$ | 16.32% |
| $B_2O_3$ | 2.34%. |

EXAMPLE 2

Eighty parts by weight of the feldspar frit prepared having the composition given in example 1 is mixed with 20 parts of $SnO_2$. The liquid is prepared from 65 parts by weight of 1,3-butanediol, 9 parts by weight of PEG 400, 24 parts by weight of glycerol, and 2 parts by weight of deionized water. The mixture of liquids is mixed in an amount of 50 parts by weight with 50 parts by weight of opaque dental porcelain powder and homogenized in a sigma-shaped kneader-mixer. To prevent segregation, 1 part by weight of Aerosil® R 972 is added. To ensure durability, 0.05 parts by weight of Acticid SPX is added.

We claim:

1. A powder composition for the preparation of an opaque dental porcelain, containing
   one or more feldspar frits comprising a number of feldspar frit components of different chemical composition and different physical properties, wherein said feldspar frit or frits have a maximum grain size of less than 20 µm, a $d_{50}$ of from 3 to 6 µm, and a $d_{90}$ of from 12 to 16 µm;
   $CeO_2$ as the opacifier, optionally additional opacifiers; and
   optionally pigments.

2. The powder composition according to claim 1 containing the optional additional opacifiers, wherein said additional opacifiers are metal oxides.

3. The powder composition of claim 2 wherein the metal oxides are $SnO_2$, $TiO_2$, and/or $ZrO_2$.

4. The powder composition of claim 1 containing the optional pigments, wherein said pigments are colored metal oxides.

5. The powder composition according to claim 1 containing
   from 30 to 65% by weight of $SiO_2$
   from 2 to 6% by weight of $Na_2O$
   from 3 to 15% by weight of $K_2O$
   from 5 to 15% by weight of $Al_2O_3$
   from 0.5 to 10% by weight of CaO
   from 0.5 to 10% by weight of $B_2O_3$, and
   from 0.5 to 50% by weight of $CeO_2$.

6. The powder composition according to claim 5, additionally containing up to 50% by weight by $TiO_2$, up to 9% by weight of $ZrO_2$, and up to 50% by weight of $SnO_2$ as further components.

7. A mixture in the form of a paste containing the composition according to claim 1 and, in addition, one or more liquids for imparting a paste-like consistency and optionally additives.

8. The mixture in the form of a paste according to claim 7, wherein said liquids are water, modeling liquids, dihydric alcohols, glycerol, polyethylene glycols, and/or silicone oils.

9. A mixture in the form of a paste, wherein the mixing ratios of liquid(s) to dry composition according to claim 1 are between 1:4 and 1:1.

10. The mixture in the form of a paste according to claim 7 further containing at least one stabilizer and/or at least one preservative as said optional additives.

11. The mixture in the form of a paste according to claim 10, wherein said stabilizer or stabilizers are
    surface-active metal oxide powders having grain sizes in the range of 5 to 40 nm;
    organic thickening agents in amounts of from 0 to 5% by weight;
    at least one complexing and/or chelating agents.

12. The mixture of claim 11 wherein the surface-active metal oxide powders are $SiO_2$, aerosils, $TiO_2$-P25, pyrogenic $ZrO_2$, and/or alumina C.

13. The mixture of claim 11 wherein the organic thickening agents are present in amounts of from 0.05 to 1% by weight.

14. The mixture of claim 11 wherein the organic thickening agents are cellulose, methylcellulose and derivatives thereof, gelatine and/or alginates.

15. The mixture in claim 11 wherein at least one complexing and/or chelating agent is citric acid.

* * * * *